(12) United States Patent
Pérez Méndez et al.

(10) Patent No.: US 6,277,403 B1
(45) Date of Patent: Aug. 21, 2001

(54) PRODUCTION OF NEW POLYMER LIQUID CRYSTALS CAPABLE OF HAVING AN INTERACTION WITH LIPOSOMES

(75) Inventors: María Mercedes Pérez Méndez; Carmen Reyes Mateo Martínez, both of Madrid (ES)

(73) Assignee: Consejo Superior de Investigaciones Cientificas, Madrid (ES)

( * ) Notice: Subject to any disclaimer, the term of this patent is extended or adjusted under 35 U.S.C. 154(b) by 0 days.

(21) Appl. No.: 09/355,090

(22) PCT Filed: Jan. 16, 1998

(86) PCT No.: PCT/ES98/00005

§ 371 Date: Sep. 22, 1999

§ 102(e) Date: Sep. 22, 1999

(87) PCT Pub. No.: WO98/31347

PCT Pub. Date: Jul. 23, 1998

(30) Foreign Application Priority Data

Jan. 20, 1997 (ES) .................................... 9700099

(51) Int. Cl.[7] .................................... A61K 1/127
(52) U.S. Cl. ........................ 424/450; 428/402.2
(58) Field of Search .................... 424/450, 121, 424/9.32, 9.51, 417, 94.3; 436/829; 935/54; 428/402.2; 264/4.1, 4.3

(56) References Cited

U.S. PATENT DOCUMENTS

| | | |
|---|---|---|
| 4,999,348 | 3/1991 | Cioca et al. . |
| 5,631,018 * | 5/1997 | Zalipsky ............................. 426/450 |
| 5,792,472 | 8/1998 | Roux et al. . |

FOREIGN PATENT DOCUMENTS

| | | |
|---|---|---|
| 486437 | 5/1992 | (EP) . |
| 486445 | 5/1992 | (EP) . |
| 509968 | 10/1992 | (EP) . |
| 40 6178930 * | 6/1994 | (JP) . |
| WO9319735 | 10/1993 | (WO) . |
| WO9420073 | 9/1994 | (WO) . |

OTHER PUBLICATIONS

Ober et al., 1982, Polymer J. 14:9–17.
Gregoriades, Liposomes in Biol. Sys., 1980, pp. 25–85.
Lasic, Liposomes from Physics to Applications, 1993, pp. 265–320.
Ringsdorf et al., 1988, Ang. Chem. Int. De. Engl. 27:116.
Galli et al., 1982, Makromol. Chem. 183:2693.
Chiellini et al., 1983, Polymer Bulletin 9:336.
Chiellini et al., 1990, Mol. Cryst. Liq. Cryst. 179:405–18.
Chiellini et al., Preprints IUPAC Symposium on Macromolecules, Amherst, 1982, pp. 365.
Bader et al., Preprints IUPAC Symposium on Macromolecules, Amherst, 1982, pp. 341.
Lasic, Chemical Review, 95(8):2605.

* cited by examiner

Primary Examiner—Gollamudi S. Kishore
(74) Attorney, Agent, or Firm—Klauber & Jackson

(57) ABSTRACT

Process comprising the following steps: (a) preparation of liposomes (bilayers) by extrusion from lipids, such as dimiristoylphosphatidylcholine; (b) preparation of polymers (−) PTOBEE ($C_{26}H_{20}O_8$)$_n$, both being liquid crystals of the cholesteric type; ( ) addition of the polymers to the suspension of liposomes. These systems have biomedical and pharmacologic applications such as 'stealth liposomes', or 'ghost liposomes', for the encapsulation of drugs with, as a result, an extension of their average life in the blood flow."

13 Claims, No Drawings

PRODUCTION OF NEW POLYMER LIQUID CRYSTALS CAPABLE OF HAVING AN INTERACTION WITH LIPOSOMES

This application is a 371 of PCT/ES/98/00005 filed Jan. 16, 1998.

FIELD OF APPLICATION

The present invention fits within a first chemical sector with biomedical and pharmacological applications.

PRIOR ART

Liquid crystals are self-organizable systems. They do not pass directly from the crystalline state to the isotropic melt, when being heated, but rather they form mesophases that combine the order of the perfect crystal with the mobility of the liquid. Their molecular base is almost always simple: they form anisotropic or amphiphilic molecules with a rigid geometry (mesogenic unity) connected to another flexible part (spacer), that package in blocks with anisotropic properties (H. Ringsdorf, B. Schlarb and J. Venzmer, "Molecular Architecture and Function of Polymeric Oriented Systems: Models for the Study of Organization, Surface Recognition, and Dynamics of Biomembranes", Ang. Chem. Int. De. Engl. 1988, 27, pp. 116). The parallel orientation of their longitudinal molecular axis is common to all mesophases. Two main types may be distinguished: Nematic (with their molecular centers distributed isotropically) and smectic (molecular centers organized in planes). The spatial arrangement of nematic planes stacked in a helicoid superstructure, characterized by a preferable chirality, is known as cholesteric mesophase. Cholesteric mesophases reflect incident light and when their helix pitch is comparable to the wavelength of the visible light, they exhibit typical bright colors.

U.S. Pat. No. 4,999,348 discloses compositions for topical use, providing controlled release and penetration of biologically active substances comprising cholesteric liquid crystals the lamellar molecular structure of which entraps the biologically active substance is entrapped. Specifically, the compositions comprise vitamin A, the cholesteric liquid crystal and a polyacrylic gel which forms a polymeric skin around the liquid crystals.

WO-A-9319735 discloses a process for preparing microcapsules or liposomes with controlled sizes which may optionally be encapsulated by polymer coatings wherein monomers capable of polymerizing within the liposomes or microcapsules are used, and wherein the whole of a microcapsule or liposome and the polymerized monomers form a liquid crystal.

The development of polymer liquid crystals followed that of monomer liquid crystals and began with polymers whose main chain, as a whole, acted as a mesogene, those prepared from a solution (lyotropic) as well as those prepared from a melt (thermotropic). Subsequently, the mesogenic units were introduced well hung from the main chain by means of a flexible spacer (of side chain) or connected all along the main chain by a flexible aliphatic spacer (of main chain).

In 1982, Lenz et al (C. Ober, J. I. Jin, R. W. Lenz, Polym. J. 1982, 14, 9) synthesized thermotropic polymer liquid crystals whose mesogenic unity, previously studied in works of low molecular weight, based on a central residue of terephthalic acid flanked by two p-oxybenzoil residue connected by flexible polymethylene spacers. High transition temperatures were obtained from transition to the mesophase and to the isotropic melt.

Galli et al. (G. Galli, E. Chiellini, C. K. Obert, R. W. Lenz, Makromol. Chem. 1982, 183, pp. 2693) in 1982 also introduced to the mesogene itself flexible spacers compatible with the aqueous system under physiological conditions, that is to say, hydrophilic spacers with a low molecular weight with hydroxy ending, of the oligo oxyethelene and olio oxypropylene type, the latter containing chiral centers in each unit. These spacers had also been used in low molecular weight liquid crystals, for the purpose of reducing the transition temperatures. The influence of the type, length and distribution of the spacers on the behavior of the formed mesophases was observed, limiting the liquid crystal nature of the polymers to 10 units in the spacer.

In 1983. Malanga et al. (C. Malanga, N. Spassky, R. Menicagly, E. Chiellini, Polymer Bulletin 1983, 9, pp. 336) extended the synthesis, using as flexible spacers optically active dioles with a different length and degree of substitution, capable not only of giving the polymers a hydrophilic nature but also the cholesteric stereochemical arrangement to the mesophase thereof. Starting with chiral glycols (an enantiomer of a specific sign) as the spacer, a polymer with the same optical sign was obtained in all cases. Starting with the racemic mixture of glycol as the spacer, a "racemic" non-chiral polymer with a nematic, never cholesteric, mesophase was always obtained (E. Chiellini, R. Po, S. Carrozzino, G. Galli and B. Gallot, "Chiral Liquid-Crystalline Polymers. IX. The Effect of Chiral Spacer Structure in Thermotropic Polyesters", Mol. Cryst. Liq. Cryst. 1990, Vol. 179, 405–418; E. Chiellini, R. Solaro, G. Leonardi, R. Lisciani, G. Mazzanti, Eur. Pat. Appln. 19, pp, EP 509968 A1 921021; E. Chiellini, R. Solaro, L. Bemporad, S. D'Antone, Eur. Pat. Appln., 11, pp, EP 486445 A2 920520; E. Chiellini, R. Solaro, L. Bemporad, Eur. Pat. Appl., 13 pp. EP 486437 A2 920520).

The nematic compound $(C_{26}H_{20}O_8)n$ obtained from the racemic mixture of the corresponding glycol of its spacer, has been described by Chiellini (E. Chiellini, R. Po, S. Carrozzino, G. Galli and B. Gallot, "Chiral Liquid-Crystalline Polymers. IX. The Effect of Chiral Spacer Structure in Thermotropic Polyesters" Mol. Cryst. Liq. Cryst., 1990, Vol. 179, 405–418), as non-toxic, compatible with blood and permeable to different solutes (E. Chiellini, G. Galli, R. W. Lenz and C. K. Ober Preprints IUPAC Symposium on Macromolecules, Amherst, 1982, p. 365). In the same study a series of polycarbonates synthesized from mixtures of Bisphenol A and oligoethers hydroxy ended with phosgene in a pyridine-dioxane solution are described. The authors affirm having synthesized gel membranes from these polycarbonates by the phase reversal technique (E. Chiellini, G. Galli, R. W. Lenz and C. K. Ober Preprints IUPAC Symposium on Macromolecules, Amherst, 1982, p. 365), achieving improved mechanical properties.

A parallelism can be established between the behavior of the liquid crystals in material science and lipids in life sciences (H. Ringsdorf, B. Schlarb and J. Venzmer, "Molecular Architecture and Function of Polymeric Oriented Systems: Models for the Study of Organization, Surface Recognition and Dynamics of Biomembranes". Ang. Chem. Int. De. Engl. 1988, 27, pp. 116).

Lipids are also self-organizable combining order and mobility. The arrangement of their amphiphilic molecules in water form liposomes, spherical two-layer or multi-layer structures that are cellular models useful to study membrane properties and cellular interactions (H. Bader and H. Ringsdorf Preprints IUPAC Symposium on Macromolecules, Amherst, 1982, p.341).

Liposomes are particularly interesting as potential agents to encapsulate sensitive biomaterials (G. Gregoriadis, A. C. Alison, eds. "Liposomes in biological systems"; John Wiley and Sons, Chichester, N.Y. (1980)). However, a severe inconvenience in the use of liposomes as a vehicle for drugs for release thereof inside the body, is their rapid ingestion by the cells of the reticuloendothelial system, varying the average life time of the liposomes in the blood, $t_{1/2}$ between minutes and dozens of minutes (D. D. Lasic, "Liposomes from Physics to Applications"; Elsevier Science Publishers B. V., Amsterdam, London, New York, Tokyo (1993)), which eliminates many of the intravenous uses of liposomes.

WO-A-9420073 discloses lipid-polymer conjugates and the combination thereof with liposomes, said conjugates comprising a vesicle-forming lipid and a polymer covalently attached to the lipid. To be able to attach to the lipid, the lipid must have a polar head group.

Different processes to lengthen the average life time of liposomes in blood have been developed. One of them is the concept of "stealth liposome", developed by Lasic (D. D. Lasic, "The Stealth Liposome", Chemical Review, Vol. 95, No. 8 (1995), 2605), where polymer chains, normally polyethyelene glycol, are grafted on the surface thereof "concealing it" and achieving some circulation times of 1 to 2 order of magnitudes longer.

The obtainment of new polymer liquid crystals capable of having an interaction with liposomes is therefore of great interest due to their potential use in the design of "ghost" liposomes." Our cholesteric liquid crystals seemed potentially capable to us at first sight.

DESCRIPTION OF THE INVENTION

As claimed, the present invention refers to a process for preparing polymer ocated liposomes, wherein the coating is prepared from one or both thermotropic polyesters, PTOBEE $(C_{26}H_{20}O_8)_n$

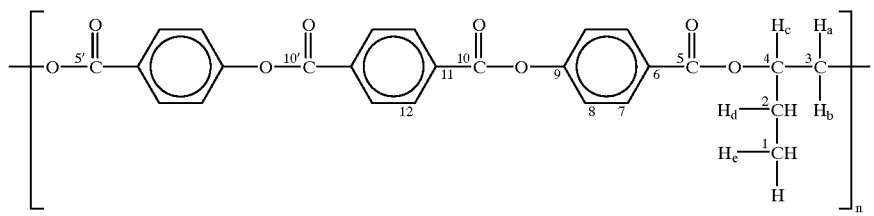

and PTOBDME $(C_{34}H_{36}O_8)_n$

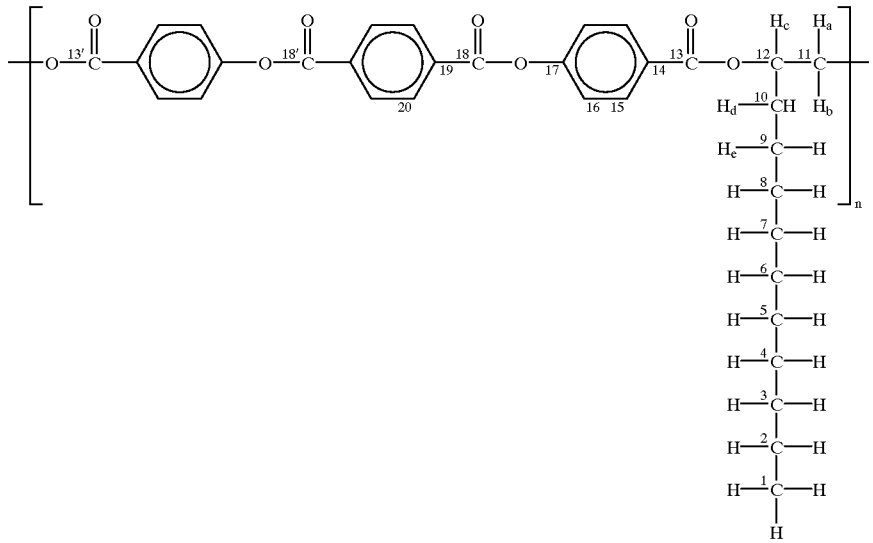

Both cholesteric liquid crystals, whose structure indicates their possible use as a liposome stabilizer. Both have proven to interact with liposomes of a certain lipid, in two-layer ones as well as multi-layer ones as evidence by the displacement of the transition of the gel to fluid (liquid crystal state) of the pure liposome.

These polymers could attach themselves to the surface of a liposome by insertion of the hydrophobic anchoring group inside the membrane.

EXAMPLE 1

In order to test the polymer-liposome interaction (two-layer) liposomes were prepared by extrusion, with a diameter of some $0.1\mu$. The selected liposome was dimyristoyl phosphatidyl choline (DMPC), a saturated chain lipid whose transition temperature from gel phase → fluid phase is 24° C.

The previously synthesized polymers (M. Perez-Mendez, C. Marco Rocha, Spanish patent no. 9700100).

a) (−) PTOBEE $(C_{26}H_{20}O_8)_n$, and b) PTOBDME $(C_{34}H_{36}O_8)_n$, both, liquid crystals of a cholesteric nature.

The polymers were added respectively to the liposome suspension in the concentrations of: 10% and 20% in each case.

The techniques chosen to study the interaction were, transmission electronic microscopy (TEM) (by the techniques of preparation of a cryomicroscopy sample and negative staining sample) and stationary state fluorescence.

The fluorescent probe used for its study by fluorescence was diphenylhexatriene (DPH). This probe was introduced into the liposome in a ratio of: 1 probe/500 lipids. By measuring the anisotropy in the stationary state of the probe in the liposome without a polymer, phase transition was detected at 24° C. Upon introducing 10% PTOBDME, whose lateral aliphatic chain is of 10 carbon atoms, this transition was displaced to 22° C. The addition of 20% PTOBDME displaced the transition to 20° C. Something similar happened upon introducing the polymer (−) PTOBEE.

We assume that the insertion of the hydrophobic aliphatic chain of the polymer between the lipid chains of the liposome and the subsequent coating of the surface of the liposome by the rigid mesogene of the liquid crystal.

These data confirmed the interaction of both polymers with the liposome (DPMC).

What is claimed is:

1. A process for preparing polymer coated liposomes, the process comprising the steps of preparing a suspension of liposomes selected from two-layer liposomes or multilayer liposomes, by extruding a lipid;

selecting a liquid crystal polymer and adding the polymer to the suspension of liposomes for providing a polymer coating to the liposomes;

wherein the polymer is selected from the group of cholesteric liquid crystals having hydrophobic groups, a rigid mesogene, a cholesteric mesophase and a capability of interacting with the liposomes, consisting of poly[oxy(ethyl-1,2-ethanediyl)oxycarbonyl-1,4-phenyleneoxycarbonyl-1,4-phenylenecarbonyloxy-1,4-phenylenecarbonyl of the formula

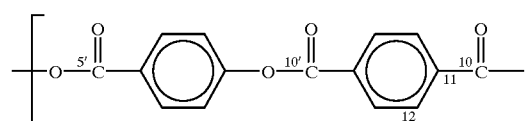

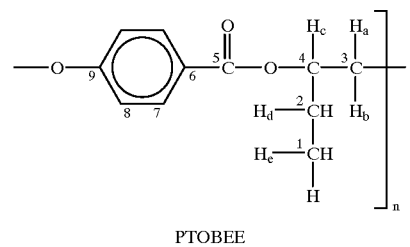

PTOBEE poly[oxy(decanyl-1,2-ethanediyl)oxycarbonyl-1,4-phenyleneoxycarbonyl-1,4-phenylenecarbonyloxy-1,4-phenylenecarbonyl] of the formula

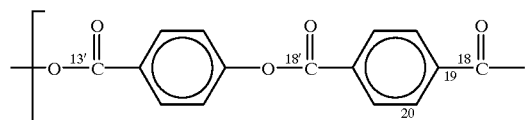

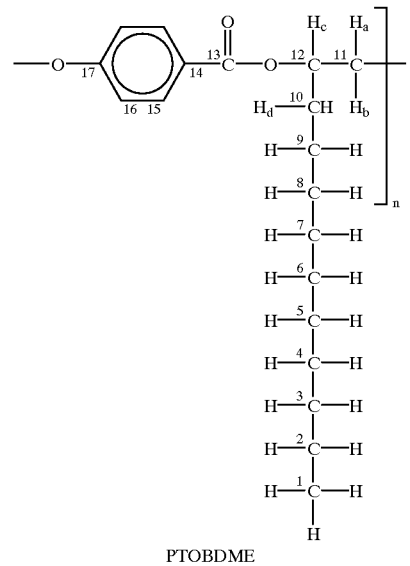

PTOBDME and mixtures thereof;

whereby polymer is added to the suspension of liposomes in a proportion of 10–20%.

2. A process according to claim 1, wherein the polymer is poly[oxy(ethyl-1,2-ethanediyl)oxycarbonyl-1,4-phenyleneoxycarbonyl-1,4-phenylenecarbonyloxy-1,4-phenylenecarbonyl.

3. A process according to claim 1, wherein the polymer is poly[oxy(decanyl-1,2-ethanediyl)oxycarbonyl-1,4- phenyleneoxycarbonyl-1,4-phenylenecarbonyloxy-1,4-phenylenecarbonyl].

4. A process according to claim 1, wherein the polymer is (−)poly[oxy(decanyl-1,2-ethanediyl)oxycarbonyl-1,4-phenvleneoxycarbonyl-1,4-phenylenecarbonyloxy-1,4-phenylenecarbonyl].

5. A process according to claim 1, wherein the lipid is dimyristoyl phopsphatidyl choline.

6. A polymer coated liposome having a membrane forming a surface and a polymer coating, the liposome originating from a suspension of liposomes selected from two-layer liposomes or multilayer liposomes prepared from a lipid by extrusion;

wherein the polymer coating is formed of cholesteric liquid crystals having hydrophobic groups, a cholesteric mesophase and a rigid mesogene, the cholesteric liquid crystals being selected from poly[oxy(ethyl-1,2-ethanediyl)oxycarbonyl-1,4-phenyleneoxycarbonyl-1,4-phenylenecarbonyloxy-1,4-phenylenecarbonyl of the formula

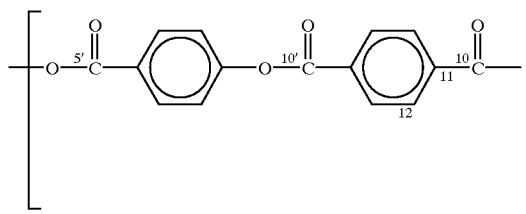

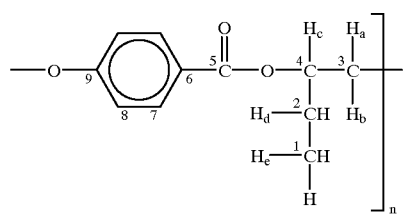

PTOBEE poly[oxy(decanyl-1,2-ethanediyl)oxycarbonyl-1,4-phenyleneoxycarbonyl-1,4-phenylenecarbonyloxy-1,4-phenylenecarbonyl] of the formula

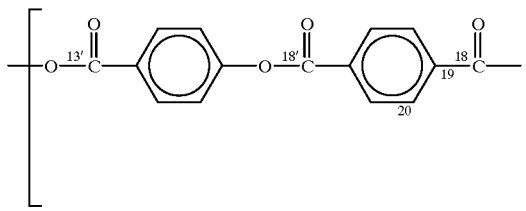

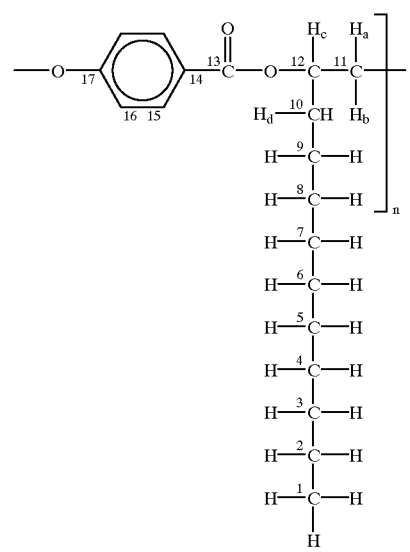

PTOBDME and mixtures thereof;

said liquid crystals being coated on the liposomes by adding the liquid crystals to the suspension of liposomes in concentrations of 10–20%.

7. A polymer coated liposome according to claim 6, wherein the liquid crystal is poly[oxy(ethyl-1,2-ethanediyl)oxycarbonyl-1,4-phenyleneoxycarbonyl-1,4-phenylenecarbonyloxy-1,4-phenylenecarbonyl.

8. A polymer coated liposome according to claim 6, wherein the liquid crystal is poly[oxy(decanyl-1,2-ethanediyl)oxycarbonyl-1,4-phenyleneoxycarbonyl-1,4-phenylenecarbonyloxy-1,4-phenylenecarbonyl].

9. A polymer coated liposome according to claim 6, wherein the liquid crystal is (−)poly[oxy(decanyl-1,2-ethanediyl)oxycarbonyl-1,4-phenyleneoxycarbonyl-1,4-phenylenecarbonyloxy-1,4-phenylenecarbonyl].

10. A polymer coated liposome according to claim 6, wherein the lipid is dimyristoyl phopsphatidyl choline.

11. A polymer coated liposome according to claim 6, wherein the hydrophobic groups of the liquid crystals are anchored within said membrane of the liposome.

12. A method for encapsulating a drug with polymer coated liposomes prepared in accordance with the process of claim 1, the method comprising adding an effective amount of the drug to the suspension of liposomes, and adding the liquid crystals to the suspension.

13. A method for encapsulating a drug with polymer coated liposomes as defined in claim 6, the method comprising adding an effective amount of the drug to the suspension of liposomes, and adding the polymer to the suspension.

* * * * *